United States Patent [19]

Theeuwes

[11] 4,418,038
[45] Nov. 29, 1983

[54] DISINFECTING WITH CHLORINE-CONTAINING BIOCIDE DISPENSED FROM SHAPED POLYMERIC BODY

[75] Inventor: Felix Theeuwes, Los Altos, Calif.

[73] Assignee: Alza Corporation, Palo Alto, Calif.

[21] Appl. No.: 317,528

[22] Filed: Nov. 2, 1981

[51] Int. Cl.³ .................... A01N 25/08; A01N 29/00
[52] U.S. Cl. .................................. 422/37; 239/54; 239/56; 424/309; 424/311; 424/325; 424/350
[58] Field of Search ............... 422/37; 424/325, 309, 424/311, 350; 239/54, 56

[56] References Cited

U.S. PATENT DOCUMENTS

| | | | |
|---|---|---|---|
| 2,990,324 | 6/1971 | Buck | 422/37 X |
| 3,142,530 | 7/1964 | Kokorudz | 422/37 X |
| 3,183,057 | 5/1965 | Marks et al. | 21/58 |
| 3,227,612 | 1/1966 | Gershon | 422/37 X |
| 3,577,532 | 5/1971 | Schneller et al. | 424/149 |
| 3,646,058 | 2/1972 | Bertin | 422/37 X |
| 3,823,873 | 7/1974 | Miller | 239/56 X |
| 3,856,932 | 12/1974 | May | 422/37 X |
| 3,858,807 | 1/1975 | Rabussier | 239/56 |
| 3,994,439 | 11/1976 | Van Breen | 239/54 |
| 4,229,410 | 10/1980 | Kosti | 422/37 X |

OTHER PUBLICATIONS

*J. Pharm. Sci.,* vol. 65, pp. 1737 to 1742; 1976; Kaminski et al., "N-Halo Derivatives V: Comparative Antimicrobial Activity of Soft N-Chloramine Systems".
*J. Chem. Soc.,* (B), Higuchi et al., pp. 546-549; 1967; "Mechanism and Thermodynamics of Chlorine Transfer among Organochlorinating Agents, Part II, Reversible Disproport. of Chloramine-T".
*J. Chem. Soc.,* (B), Higuchi et al., "Mechanism of Chlorination of Cresol by Chloramine-T. Mediation by Dichloramine-T"; 1967; 549-552.
*J. Chem. Soc.,* (B), Higuchi et al., pp. 1031-1036; 1968; "Mechanism & Thermodynamics of Chlorine Transfer among Organo-chlorinating Agents. Part III . . .".
*J. Chem. Soc.,* (B), Higuchi et al., pp. 626-631; 1969; "Mechanism & Thermodynamics of Chlorine Transfer among Organohalogenating Agents. Part IV. Chlorine Potentials & Rates of Exchange."
*J. Chem. Soc.* (B), 1969; Pitman et al., pp. 1230-1232; "Prediction of Chlorine Potentials of N-Chlorinated Organic Molecules".
*J. Pharm. Sci.,* Kosugi et al., vol. 65, No. 12, pp. 1743-1746; 1976; "N-Halo Derivatives VI; Microbiological and Chemical Evaluations of 3-Chloro-2-oxazolidinones."
*J. Med. Chem.,* Bodor et al., vol. 23, No. 5, pp. 469-474; 1980; "Soft Drugs 1 Labile Quaternary Ammonium Sales as Soft Antimicrobials."

*Primary Examiner*—Sidney Marantz
*Attorney, Agent, or Firm*—Paul Sabatine; Edward L. Mandell; Steven F. Stone

[57] ABSTRACT

Devices for dispensing a chlorine biocide. The devices disclosed are (a) a device comprising a polymer containing a chlorine donating reagent and chlorine accepting reagent that on their release react to produce a chlorinous biocide, and (b) a device comprising a polymer containing a biocide containing chlorine. A process for using the devices for controlling micro-organisms.

9 Claims, 2 Drawing Figures

DISINFECTING WITH CHLORINE-CONTAINING BIOCIDE DISPENSED FROM SHAPED POLYMERIC BODY

FIELD OF THE INVENTION

This invention pertains to a device and to a method for disinfecting articles of manufacture and for controlling the presence of unwanted microorganisms in selected environments of use. More particularly, the invention pertains to a device that (a) produces a biocide containing chlorine in the environment of use, or (b) releases a biocide containing chlorine, which biocide in (a) or (b) is useful for achieving the intended results.

BACKGROUND OF THE INVENTION

A long standing need exists in the pharmaceutical, medical, hospital, home, military, commercial and industrial fields for a desirable and effective device and method useful for controlling the presence of unwanted microorganisms in all kinds of environments, and for maintaining certain articles of manufacture free thereof. One biocide useful for this purpose is a biocide containing chlorine as disclosed in U.S. Pat. No. 3,183,057 by patentees Marks et al. In this patent, there is disclosed chlorinous gases, especially nitrogen trichloride, including monochloramine, for use in large areas such as railroad freight cars, trucks, storage rooms and the like for the preservation of fruit products. The preferred chlorine compound is nitrogen trichloride and it is used by the patentee for inhibiting the decay of fruit by spores and fungus by releasing the gas. While this procedure can be useful in certain applications, it also has disadvantages for disinfecting selected environments and articles of manufacutre, for example, the procedure lacks continuous controlled and sustained release, as the reaction between the components would go to completion upon exposure to the article of this patent to a liquid, such as in a water-moist environment. This process gasses the atmosphere even when the gas may not be needed, and the patent does not suggest a device for producing a biocide containing chlorine in the environment of use of a controlled rate and released in known biocidal amounts.

Similarly, in U.S. Pat. No. 3,577,532 issued to Schneller et al, two reagents, chlorine and ammonia are made to react for producing a product that includes monochloramine. The product is useful for controlling deterioration by microbiological attack in pharmaceutical preparations. The process in this patent for generating monochloramine consists of a two-step addition process, wherein one of the reagents is always the gas ammonia. That is, the patent does not disclose a formulation containing two or more solid reagents that can react and generate in situ a biocide containing chlorine for disinfecting environments and articles of manufacture. Also, in *J. Pharm. Sci.*, Vol. 65, pages 1737 to 1742, 1976, Kaminski et al disclosed chlorine compounds having antimicrobial activity; however, the disclosures do not teach the compounds can be used in a dispensing device and releases therefrom at controlled rates for the present purposes.

In light of the above presentation, it is apparent a need exists for a device useful for generating a biocidal compound containing chlorine, and for a device that can deliver a compound containing chlorine at a controlled rate for extended periods of time. There is a need particularly for a device that is not subject to the difficulties known to the prior art. The need also exists for a device which delivers a biocidal containing chlorine that is useful for controlling the presence of unwanted micro-organisms.

OBJECTS OF THE INVENTION

Accordingly, it is an immediate object of this invention to make available to the art a device for generating a biocide containing a chlorine functionality for controlling the presence of unwanted micro-organisms, and which device overcomes the shortcomings associated with the prior art.

Another object of the invention is to provide a device that can dispense a biocide containing chlorine useful for disinfecting an environment or an article of commerce.

Still another object of the invention is to make available a biocidal dispensing device that is inexpensive, reliable, easy to use and efficient for controlling the presence of unwanted micro-organisms in assorted environments and on various manufactures.

Yet still another object of the invention is to provide a device that can provide biocidal protection at a controlled rate and over a prolonged period of time.

Still yet another object of the invention is to provide a device that represents an improvement in the biocidal art and which device can be used for controlling the presence of unwanted micro-organisms in patient-care apparatus, and in the medico-surgical arts.

Other objects and advantages of the present invention, it is believed, will be more apparent from the following detailed description of the disclosure, the drawings and the accompanying claims.

SUMMARY OF THE INVENTION

This invention concerns (a) a device comprising a polymer containing a chlorine donating reagent, and a chlorine accepting reagent, that on their release from the polymer react in the presence of moisture to produce a chlorinous biocide, and (b) a device comprising a polymer containing a biocide containing chlorine, that on its release from the device, in (a) or (b) are useful for controlling micro-organisms in preselected environments, or on articles of manufacture.

BRIEF DESCRIPTION OF THE DRAWINGS

In the drawings, which are not drawn to scale, but are set forth to illustrate various embodiments of the invention, the Figures are as follows.

In the drawings and in the specification, like parts in related Figures are identified by like numbers. The terms appearing earlier in the specification and in the description of the drawings, as well as embodiments thereof, are further described elsewhere in the disclosure.

DETAILED DESCRIPTION OF THE DRAWINGS

Figure 1:
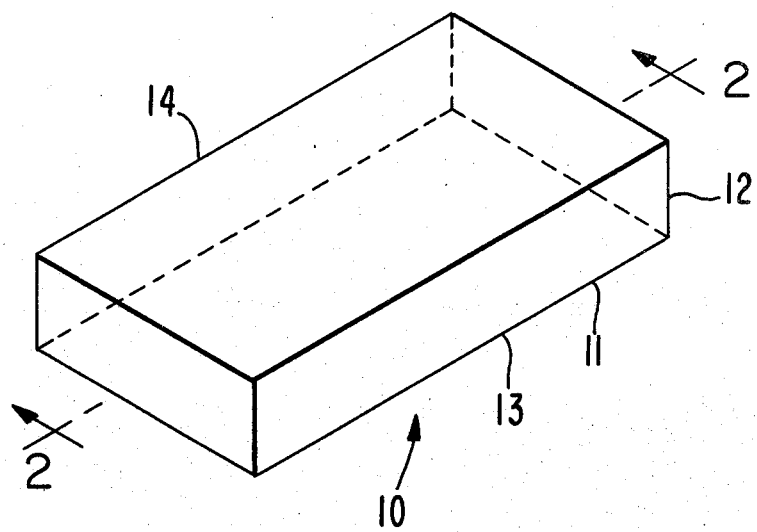
FIG. 1 is a side and top view of a dispensing device made according to the invention, and which device can be used for generating an active biocide, and also for dispensing a biocide; and, FIG. 2 is a cross-sectional view through 2—2 of FIG. 1 depicting the interior structure of the dispensing device.

Turning now to the drawings in detail, which are examples of a new and useful system for delivering a biocide, and which examples are not to be construed as limiting the invention, one device is indicated in FIG. 1 by the numeral 10. In FIG. 1, device 10 is a dispensing device and it consists essentially of a body 11 shaped, sized and adapted for placement in an environment of use, or for disinfecting an article of manufacture. Device 10 has at least one surface 12, 13 or 14, for releasing its contents, as seen in detail in FIG. 2, that leads to the intended results. Body 11 can embrace any preselected geometric shape, such as square, round, rectangle, triangle, crescent, circle and like appearances. Device 10 can be manufactured as a sheet, film, strip, rod, solid matrix, sponge, prisim, container, or capsule, and it can possess various cross-sections such as cruciform, hexagonal, or the like. In the embodiment illustrated in FIG. 1, device 10 is a solid matrix and it has a large exposed surface area for dispensing large amounts of its contents to the environment of use. Device 10 optionally is sized to fit the need and it can be from 0.1 to 16 centimeters thick, or larger, from 0.1 to 20 centimeters long, or larger, and from 0.1 to 20 centimeters in width or more. The device can be manufactured for use over a couple of hours, or for a prolonged period of time such as 30 to 40 days, or longer.

Figure 2:
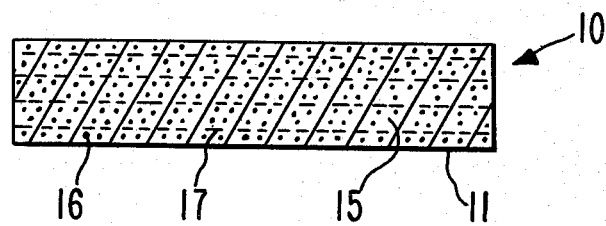

Referring to FIG. 2, dispensing device 10 is seen in cross-section through 2—2 of FIG. 1. In FIG. 2, the term member, as used herein, denotes a compound containing a chlorine functionality and is a biocide, a compound that can supply chlorine and is a chlorine donating reagent, and a compound that accepts chlorine and is a chlorine accepting reagent. The term reagent indicates a substance possessing chemical activity and used in preparing a product. The term agent denotes a biocide used for disinfecting, sterilizing, and the like. As seen in FIG. 2, device 10 comprises a body 11 formed of a polymer 15. Polymer 15 houses member 16 represented by dots, which member 16 is a biocide containing a chlorine functionality, or member 16 is a chlorine donating reagent. When member 16 is a chlorine donating reagent, polymer 15 also houses a chlorine accepting reagent 17, as represented by dashes. The chlorine donor reagent 16 and the chlorine acceptor reagent 17 on their release from device 10 into a fluid environment react to produce a biocidal agent containing chlorine. Polymer 15 comprising the body of device 10 can be formed of a polymer that releases its members by the process of diffusion, by the process of osmotic bursting, or it can be an erodible polymer that releases its members by erosion over time.

DETAILED DESCRIPTION OF THE INVENTION

Device 10, used for the purpose of the invention, comprises a body 11 formed of a polymeric material 15 that can release its members over time. Representative polymers suitable for forming body 11 for releasing members 16 and 17 by diffusion or osmotic action include acrylic polymers and copolymers of methacrylate, ethylacrylate, ethylmethacrylate, and methylmethacrylate; homopolymers and copolymers of vinyl chloride including vinyl chloride-vinyl acetate copolymer; chlorinated vinyl chloride; polyethylene; polypropylene; ethylene-propylene copolymer; chlorinated polyethylene; ethylene-vinyl acetate copolymer; styrene-butadiene copolymer; acrylonitrile-styrene-butadiene terpolymer; polyvinylidene chloride; vinyl chloride-vinylidene chloride copolymers; vinylidene chloride-acrylonitrile copolymer; vinylidene chloride-acrylate ester copolymer; polybutylene terphthalate; vinyl chloride-acrylate ester copolymer; polyvinyl acetals such as polyvinyl formal, polyvinyl acetal and polyvinyl butyral; polyethers, polyesters; polyurethanes; polyamides; chlorosulfonated polyolefins; polyisoprene; polybutadiene; silicone, and the like.

Representative of erodible polymers for manufacturing body 11 include polyesters of the general formula [—O—(W)—CO—]$_y$ wherein W is a lower alkylene of 1 to 7 carbons and in a presently preferred embodiment includes a member selected from the group consisting of alkylenes of the formula —CH$_2$—, or —CH$_2$—CH$_2$—, and y has a value such that the molecular weight of the polymer is from about 4,000 to 100,000. The polymers are polymerization-condensation products of monobasic hydroxy acids of the general formula $C_nH_{2n}$(OH)-COOH, wherein n has a value of 1 to 7, preferably 1 or 2, and the acid is preferably lactic acid or glycolic acid. Also included are the copolymers derived from mixtures of these acids. Several procedures are available for preparing the polymers as reported by Filachione et al, *Industrial Engineering Chemistry*, Vol. 36, No. 3, pages 223 to 228, 1944; Tsurcita et al, *Macromol. Chem.*, Vol. 75, pages 211 to 214, 1975; and in U.S. Pat. Nos. 2,668,162; 2,703,316; 2,767,945; and 3,297,033.

Representative of erodible polymers that can be used for the present purpose are polymers possessing a poly(orthoester) structure of the general formula:

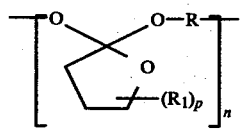

wherein R is an alkylene of 1 to 12 carbons, a cycloalkylene of 5 to 6 carbons, optionally substituted with an alkylene of 1 to 7 carbons, and an alkyleneoxy of 1 to 7 carbons; R$_1$ is a lower alkyl of 1 to 7 carbons, n is 10 to 200,000, and p is 0 or 1. The poly(orthoesters) are known in Belgian Patent No. 837,935, Netherlands Patent No. 7,600,881 and West Germany Patent No. 2,602,994.

The phrase chlorine donating reagent as used herein denotes a compound containing chlorine, which chlorine is present, or can be considered to be present, and/or yields chlorine in the positive valence state, that is, in cationic form as the chlorium ion Cl$^+$. For the most part, these compounds are those in which chlorine is attached directly to an electronegative nitrogen, oxygen or sulfur atom. Suitable active chlorine containing compounds are generically various N-chloro compounds, hypochlorites and chlorates. Specific examples of active chlorine donating compounds suitable for forming the novel delivery devices of the invention are N-chloro primary and secondary amines, N-chloro amides, N-chloro imides, heterocyclin N-chloro compounds, aromatic N-chloro compounds, and the like. Specific examples include heterocyclic N-chloro imides such as trichloroisocyanuric acid; dichloroisocyanuric acid; sodium dichloroisocyanurate; potassium dichloroisocyanurate; N-chlorosuccinimide; N-chloromalonimide; N-chlorophthalimide; and N-chloronaphthalimide. Additional suitable imides are the hydantoins such as 1,3-dichloro-5,5-dimethyl hydanatoin; N-monochlor-5,5-dimethylhydantoin; methylene-bis(N-chloro-5,5-dimethylhydantoin); 1,3-dichloro-5-methyl-5- isobutyhydantion; 1,3-dichloro-5-methyl-5-ethylhydantoin; 1,3-dichloro-5,5-diisobutylhydantoin; and the like. Also, N-chlorourea; N-chloroacetyl urea; and the like. Other useful reagents like N,N-dichloro-p-toluene sulfonamide, N,N-dichloro-benzoylurea and the like. Chlorine donating compounds wherein the carbonyl oxygen is replaced by sulfur such as dichloroamine B, monochloramine T, dichloroamine T, and the like. Various other chlorine donating compounds include chloromelamines such as trichloromelamine; pentachloromelamine; hexachloromelamine; $N,N^1$-dichloroazodicarboamidine; p-sulfone dichloramidobenzoic acid; N-chloro-biuret; 1,1-dimethyl-2-chlorobiguanide; benzenediazonium perchloride; and the like. Also, suitable chlorine donating reagents wherein the chlorine is in a positive valence state as examplified by chlorine bonded to oxygen, such as hypochlorites, chlorates, and derivatives thereof. Examples of chlorine compounds of this type include hypochlorites and chlorates of alkali and alkaline earth metals such as calcium hypochlorite, sodium hypochlorate, lithium hypochlorite, barium chlorate, potassium chlorate, sodium chlorate, and alkyl hypochlorites of up to twenty carbon atoms such as n- and iso-propyl hypochlorite, n-, sec- and tert-butyl hypochlorite, hexadecyl hypochlorite, sec-octadecyl hypochlorite; and the like.

Representative of chlorine accepting reagents useful for the purpose of the present invention are compounds that can supply ammonium ion, or serve as a nitrogen containing compound that can supply ammonium ion, or serve as a nitrogen containing compound that can act as a chlorine accepting reagent, or its functional equivalent in at least a stoichiometric amount based on the amount of available chlorine, or in the presence of an excess thereof for the production of ciocidal chloramine products, which in a presently preferred embodiment have a molecular weight of 51 to 121, such as monochloramine, and the like. Reagents suitable for this purpose that in presence of moisture can contact and react with the chlorine donor to produce a biocidal chlorine disinfectant include ammonium chloride, ammonium sulfate, ammonium alum, ammonium dihydrogen phosphate, diammonium phosphate, ammonium carbonate, urea, sulfamic acid, monoethylamine, dimethylamine, dipropylamine, morpholine and dialkylamine derivatives thereof wherein the alkyl is a straight or branched chain of 1 through 6 carbon atoms, piperidine and dialkylamine derivatives thereof wherein the alkyl group is a straight or branched chain and contains 1 through 6 carbons, and the like. Typical alkyl groups include methyl, ethyl, propyl, isopropyl, tert-butyl, neopentyl, and the like. The amount of chlorine donating reagent housed in the device can vary depending on the need, and it will usually be about 0.1% to 35% by weight based on the weight of the dispensing device. The amount of chlorine accepting reagent housed in the device can vary depending on the need, and it will usually be about 0.1% to 35% by weight based on the weight of the dispensing device. The combined amount of chlorine donating reagent and chlorine accepting reagent will be about 0.2% to 70% by weight with the remaining weight the polymeric material. The mechanism and the thermodynamics of chlorine transfer are disclosed in *J. Chem. Soc.*, (B), Higuchi et al, pages 546 to 549, 1967; *J. Chem. Soc.*, (B), Higuchi et al, pages 549–552, 1967; *J. Chem. Soc.*, (B), Higuchi et al, pages 1031 to 1036, 1968; *J. Chem. Soc.*, (B), Higuchi et al, pages 626 to 631, 1969; and *J. Chem. Soc.*, (B), Pitman et al., pages 1230 to 1232, 1969.

The biocide compounds containing a chlorine moiety operable for the purpose of this invention are represented by the following general formula:

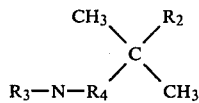

wherein $R_2$ is a member selected from the group consisting essentially of $CO_2R_5$ and $CH_2O_2CR_5$ wherein $R_5$ is an alkyl group of 1 to 20 carbon atoms, and an alkylene dioxy of 1 to 7 carbons; $R_3$ and $R_4$ are the same or different selected from the group consisting of chlorine, hydrogen and alkyl of 1 to 20 with at least one of $R_2$ and $R_1$ chlorine; and the acid addition salts. Representative alkyl group are $CH_3$; $CH_2CH_3$; $(CH_2)_2CH_3$; $C(CH_3)_3$; $(CH_2)_4CH_3$; $(CH_2)_6CH_3$; $(CH_2)_7CH_3$; $(CH_2)_{11}CH_3$; $(CH_2)_{17}CH_3$; and the like. Representative alkylenedioxy include $(CH_2)_2O(CH_2)_2O(CH_2)_2CH_3$; $(CH_2)_2O(CH_2)_2CH_3$; $CH_2O(CH_2)_2CH_3$; and the like. Representative acid addition salts include hydrochloric HCl, and the like. The chlorine compounds are disclosed in *J. Pharm. Sci.*, Kaminski et al., Vol. 65, No. 12, pages 1737 to 1742, 1976; and, *J. Med. Chem.*, Bodor et al., Vol. 23, No. 5, pages 469 to 474, 1980. The amount of biocidal chlorine agent is about 0.02% to 70% by weight.

Additional biocidal compounds containing chlorine that can be made into a device comprising a body formed of a polymer containing the chlorine biocide that is released in an effective amount into the environment of use and releases its chlorine for its biocidal activity include N-chloromalonimide; N-chlorophthalimide; N-chloronaphthalimide; N-chlorophthalimide; N-chloronaphthalimide; N-chlorourea; N-chloroacetylurea; N-N-dichlorobenzoylurea; N-N-dichloro-p-toluene sulfonamide; pentachloromelamine; hexachloromelamine; N,N-dichloroazodicarboamidine; N-chlorobuiret; dimethyl-2-chlorobiguanide; and benzene-diazonium perchloride.

The devices also can contain a surfactant that aids in the manufacture of the device and aids in increasing the release of active reagents or a biocide from the device. The surfactants can be cationic, anionic or nonionic. Exemplary cationic surfactants include lauryldimethylammonium chloride, p-diisobutylphenoxyethoxyethyldimethylbenzylammonium chloride, alkyldimethylbenzylammonium chloride, laurylisoquinolinium bromide, cetylethylammonium bromide, stearyldimethylbenzylammonium chloride, N-soya-N-ethylimorpholinium-ethosulphate, N(acyl-colamionoformylmethyl) pyridinium chloride, a mixture comprising alkyl ($C_9H_{19}$ to $C_{15}H_{31}$) tolylmethyltrimethylammonium chloride and laurylisoquinolinium bromide, coamiodoalkylbetaine, and N-laurylmyristyl-aminopropionic acid. Exemplary anionic surfactants include linear alkylaryl sulfonates prepared by Friedel-Crafts reaction of an olefin and benzene wherein the olefin has from 10 to 18 carbon atoms, and the alkali metal salts thereof, and other anionic surfactants such as alkylaryl sulphonate, capryl imidazoline derivatives, dioctylester of sodium sulphosuccinic acid, sodium lauryl sulfate, sodium salt of alkylated aryl polyether sulphate, triethanolamine salt of lauryl sulphate, triethanolamine salt of alkylaryl sulphonate, and mixtures thereof. Exemplary nonionic surfactants include alkylated aryl polyether alcohol, polyethylene glycol tertdodecyl thioether, fatty acid amind condensates, aromatic polyglycol ether condensates, secondary amide of lauric acid, fatty acid alkanolamine condensates, sorbitan monolaurate, sorbitan nonlaurate polyoxyethylene, sorbitan mono-oleate, sorbitan mono-oleate polyoxyetheylene deriative, mannide mono-oleate polyoxyethylene laurylether, polyoxyethylene esters of mixed resins and fatty acids, and mixtures thereof, and surfactants generically including the condensation product of a linear aliphatic alcohol having from 8 to 22 carbon atoms in its aliphatic portion and an alkylene oxide wherein the oxide constitutes from about 55 to 80% by weight of the surfactant molecule. Examples of surfactants identified by trademarks include Igepal® CO-710 a nonionic consisting essentially of nonyl phenol condensed with 10 to 11 mols of ethylene oxide; Pluronic® P-65 a nonionic consisting essentially of hydrophilic polyoxyethylene groups and a hydrophobic polyoxypropylene group having an average molecular weight of 3500 with 50% ethylene oxides; Pluronic® P-123 a nonionic with a molecular weight of about 5650 with 30% ethylene oxide groups; Deriphat® 160 an ampholytic disodium N-Lauryl-B-imino-di-propionate, and the like. The amount of surfactant used is an amount sufficient to achieve the intended results, normally, the amount will range from 0.01% to about 5% by weight, based on the total weight of all the components in the device.

The expression "controlling the presence of micro-organisms" as used herein, means in the general context of this invention, killing, preventing and/or retarding the presence or the propagation of micro-organisms in a pre-selected environment of use or for sterilizing or disinfecting an article of manufacture. The term "environment of use" includes positioning the device in pre-selected areas such as hospital rooms, clinics, laboratories, animal quarter, bathrooms, swimming pools, fumigate stored citrus fruits in railroad cars and warehouses, irrigation canals, animal dips, and the like. The term "article of manufacture" includes germ-free boxes, cans, garment bags, mattresses, urine containers, surgical instruments, barber tools, garbage cans, catheters, and like articles in need of disinfecting thereof.

The term biocide as used herein includes microcide and disinfectant, and it refers to the generation of the chloro-biocide or the delivery of a chloro-biocide into the environment of use, or brought into contact with an article of manufacture to kill, cleanse, prevent and/or retard the presence, or the propagation of harmful or unwanted micro-organisms. The micro-organisms include the fungi *Aspergillus niger, Aspergillus flavus, Phizopus nigricans, Cladosporium herbarium, Epidermophyton flouosum, Trichophyton mentagrophytes, Histoplasma capsulatum*, and the like. The term micro-organisms also include antibacterial activity against *Pseudomonas aeruginosa, Escherichia coli, Proteus vulgaris, Staphyloccus aureus, Staphyloccus albus, Streptococcus faecalis, Klebsiella, Enterobacter aerogenes, Proteus Mirabilis, Nisseria catarrhalis, Bacillis subtilis, Seratia marcescens, Dysentery bacilli*, and other gram-negative, and gram-positive bacteria, mycobactin, and the like. The term also embraces yeasts such as *Saccharomyces cerevisiae, Saccharomyces ellipsoidues, Candida albicans*, and the like. Additionally, spores of micro-organisms and viruses such as *Aspergillus glaucus, Mucor racemosus, Oospora lactis*, bacteriophase, and the like are within the intent of the invention.

The devices containing the biocide, or chlorine donor and chlorine acceptor leading to generating the biocide containing chlorine, are used for their disinfectant activity generally in a fluid atmosphere. The term fluid atmosphere includes an atmosphere containing moisture, and the term fluid includes water, buffers, and the like, and moisture denotes water.

The following examples will serve to further illustrate the present invention, but the invention is not intended to be limited thereto.

EXAMPLE 1

A dispensing device of rectangle shape and comprising a solid matrix body containing a chlorine donating reagent and a chlorine accepting reagent for producing a chlorinous biocide in an aqueous environment is prepared as follows: first, 1000 mg of N-chlorosuccinimide is blended into 3000 mg of dry ethylene-vinyl acetate copolymer having a vinyl acetate content of 28% on a two-roller rubber mill. Next, 1000 mg of dry ammonium chloride is thoroughly mixed with 3000 mg of ethylene vinyl-acetate copolymer having a vinyl acetate content of 28% on a two-roller rubber mill.

Next, 25 mg of N-chlorosuccinemidimide and 25 mg of the ammonium chloride polymer blends are thoroughly blended for 10 to 15 minutes at 25° to 35° C. on the two-roller mill to produce a film having a homogenous dispersion of the two blends. Then, the film is ground in a rotary knife grinder to produce particle sized 1/16 to ⅛ inches, average size, and the particles then transferred to an extruder. Finally, the particles are extruded through a dye at 60° C. to yield the dispensing device. The device releases the reagents by diffusion in a moist environment with the reagents reacting to yield a chlorinous biocide. The device is stored in a dry package to prevent premature contact with moisture.

EXAMPLE 2

A dispensing device of rod shape and comprising a solid matrix body containing a chlorine donating reagent and a chlorine accepting reagent for producing a chlorinous biocide in an aqueous environment is prepared as follows: first, 4000 mg of N-chlorosuccinimide is blended into 1000 ml of dry chloroform, and the mixture again blended to form a granulate. The granulate is sieved through a standard No. 14 mesh sieve and is dried at 35° C. for 6 to 8 hours. Next, 4000 mg of dry ammonium chloride is thoroughly mixed with dry methanol to yield a blend. The blend is sieved through a No. 14 mesh sieve and dried at 100° C. for about 6 hours.

Next, 20 mg of the N-chlorosuccinimide and 20 mg of the ammonium chloride are blended for 10 to 15 minutes at 25° to 35° C. on a two-roller mill with 60 mg of ethylene vinyl-acetate copolymer having a vinyl acetate content of 28% to produce a film having a homogenous dispersion of the two reagents. Then the film is ground in a rotary knife grinder to produce particle sized 1/16 to ⅛ inches, average size, and the particles then transferred to an extruder. Finally, the particles are extruded through a dye at 60° C. to yield the dispensing device. The device releases the reagents by diffusion in a moist environment with the agents reacting to yield a chlorinous biocide. The device is stored in a dry package to prevent premature contact with moisture.

EXAMPLE 3

A device that functions as a chlorinous generator is made by repeating the procedure of Example 2 with the conditions as set forth and werein the chlorine donating reagent is N-chlorosuccinimide and the chlorine accepting reagent is dimethylamine hydrochloride. The reagents on release from the polymeric matrix generate a chlorine biocide for disinfecting in an aqueous medium articles of manufacture.

EXAMPLE 4

A device for dispensing a biocide having a chlorine functionality, which device comprises a body having a disc shape which is manufactured as a solid matrix containing the biocide is made as follows: first, 45 mg of n-hexyl-α-N,N-dichloromino-isobutyrate is fed to a two-roller mill previously charged with 55 mg of ethylene vinyl-acetate copolymer having a vinyl acetate content of 28%. The biocide and the copolymer are blended for 10 to 15 minutes at about 25° C. to produce a homogenous film. Next, the film is cut into pieces, fed to an extruder to yield the rod shaped device. The preparation of the chlorine derivative is disclosed in *J. Pharm. Sci.*, Kaminski et al., Vol. 65, No. 4, page 553 to 557, 1976.

EXAMPLE 5

A device for dispensing a biocide is made as follows: first, 15 mg of trichlorotriaminotriazine, 30 mg of sodium sulfate, 0.1 mg surfactant Aerosol-OT, and 55 of powdered microporous polypropylene are blended into a homogenous blend, then 45 mg of ammonium chloride, 0.1 mg of Aerosol-OT and 55 mg of microporous polypropylene are blended into a homogenous blend. Next, the two blends are blended into a homogenous mass, and pressed into a film under a pressure of 4000 lb/sq. in., to yield a device useful for the intended purpose.

It will be understood by those versed in the disinfectant art, that in the light of the present specification, and the accompanying claims, many embodiments of the invention can be made without departing from the spirit of the invention.

The claims:

1. A process for disinfecting an article of manufacture, which process comprises placing the article in the presence of a device, which device comprises a body of a polymer containing a biocide of the formula:

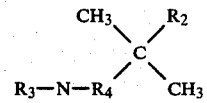

wherein $R_2$ is a member selected from the group consisting of $CO_2R_5$ and $CH_2OCR_5$, wherein $R_5$ is a member selected from the group consisting of alkyl of 1 to 20 carbons, and an alkylenedioxy of 1 to 7 carbons; $R_3$ and $R_4$ are selected from the group consisting of chlorine, hydrogen and alkyl with at least one of $R_3$ and $R_4$ chlorine; and the acid addition salts; which biocide on its release from the device and in the presence of moisture contacts the article for disinfecting same.

2. The process for disinfecting an article of manufacture according to claim 1 wherein the article is a urine container.

3. A device for dispensing a biocide to an environment of use, the device comprising a body shaped, sized and adapted for easy placement in the environment and having at least one surface exposed to the environment, said body formed of a polymeric material containing a biocide of the formula:

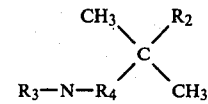

wherein $R_2$ is a member selected from the group consisting of $CO_2R_5$ and $CH_2OCR_5$, wherein $R_5$ is a member selected from the group consisting of alkyl of 1 to 20 carbons, and an alkylenedioxy of 1 to 7 carbons; $R_3$ and $R_4$ are selected from the group consisting of chlorine hydrogen and alkyl of 1 to 20 carbons with at least one of $R_3$ and $R_4$ chlorine; and the acid addition salts thereof; and wherein, when the device is in the environment, it releases at the surface a biocidally effective amount of the biocide for controlling the presence of microorganisms in the environment of use over a prolonged period of time.

4. A device for disinfecting an article of manufacture, the device comprising a polymer containing a biocide of the general formula:

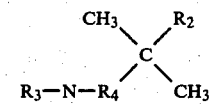

wherein $R_2$ is a member selected from the group consisting of $CO_2R_5$ and $CH_2OCR_5$, wherein $R_5$ is a member selected from the group consisting of alkyl of 1 to 20 carbons and an alkylenedioxy of 1 to 7 carbons; $R_3$ and $R_4$ are selected from the group consisting of chlorine and hydrogen with at least one of $R_3$ and $R_4$ chlorine; and the acid addition salts thereof; and wherein when the device is in operation, it releases a biocidally effective amount of the biocide for disinfecting said article.

5. The device for disinfecting the article of manufacture according to claim 4 wherein the article is a urinary container.

6. The device for disinfecting the article of manufacture according to claim 4 wherein the article is a urinary container and the device releases the biocide in the presence of moisture.

7. A device for dispensing a biocide to an environment of use, the device comprising:
(a) a body shaped, sized, and adapted for placement and retention in the environment of use, and having at least one surface area for dispensing a biocide, said body formed of a polymeric material that maintains its integrity in the environment; and,
(b) a biocide in the polymeric material, said biocide a member selected from the group consisting of N-chloromalonimide, N-chlorophthalimide and N-chloronaphthalimide, which biocide is released in a biocidally effective amount to the environment of use over time.

8. A device for dispensing a biocide to an enviornment of use in need of a biocide, the device comprising:
(a) a body shaped, sized and adapted for placement and retention in the environment of use, and having at least one surface for dispensing a biocide, said body formed of a polymeric material that maintains its integrity in the environment of use; and, (b) a biocide in the polymeric material, said biocide a member selected from the group consisting of N-chlorourea, N-chloroacetylurea, and N,N-dichlorobenzoylurea, which biocide is released in a biocidally effective amount to the environment of use over time.

9. A device for dispensing a biocide to an environment of use in need of a biocide, the device comprising:

(a) a body shaped, sized and adapted for placement and retention in the environment of use, and having at least one surface for dispensing a biocide, said body formed of a polymeric material that maintains its integrity in the environment of use; and, (b) a biocide in the body in an amount for controlling the presence of micro-organisms in the environment of use, the biocide a member selected from the group consisting of pentachloromelamine and hexachloromelamine, which biocide is released in a biocidally effective amount to the environment of use over time.

* * * * *